Figure 1A:
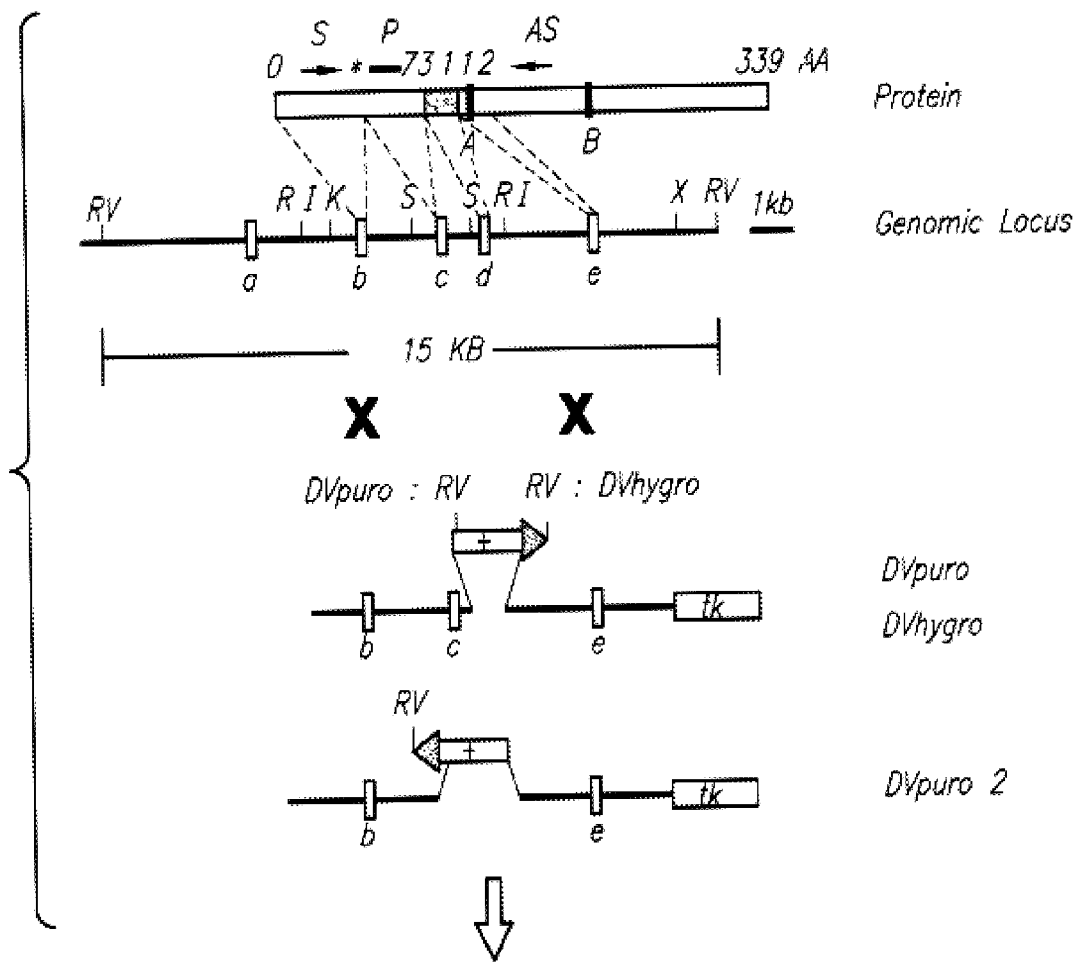

US006057489A

United States Patent [19]
Hasty et al.

[11] Patent Number: 6,057,489
[45] Date of Patent: *May 2, 2000

[54] MMRAD51-DEFICIENT CELLS AND TRANSGENIC MICE

[75] Inventors: Paul Hasty, Magnolia; Dae-sik Lim, Houston, both of Tex.

[73] Assignee: M.D. Anderson Cancer Center, Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/710,117

[22] Filed: Sep. 12, 1996

[51] Int. Cl.7 ............................... C12N 5/09; C12N 5/63; C12N 5/00; C12N 15/00
[52] U.S. Cl. .................................. 800/18; 800/21; 800/22; 800/25; 800/3; 435/455; 435/463; 435/325; 435/354; 435/320.1; 435/6
[58] Field of Search ..................................... 800/2, 18, 21, 800/22, 25, 3; 435/172.3, 320.1, 69.1, 91.2, 325, 455, 463, 6, 354; 935/23, 78, 79, 81, 70, 71; 536/23.5

[56] References Cited

U.S. PATENT DOCUMENTS

| | | | |
|---|---|---|---|
| 5,347,075 | 9/1994 | Sorge | 800/2 |
| 5,464,764 | 11/1995 | Capecchi et al. | 435/172.3 |

FOREIGN PATENT DOCUMENTS

| | | |
|---|---|---|
| 0 386 563 A1 | 2/1990 | European Pat. Off. . |
| WO 90/13641 | 11/1990 | WIPO . |
| WO 91/04753 | 4/1991 | WIPO . |
| WO 91/09865 | 7/1991 | WIPO . |
| WO 911535 | 8/1991 | WIPO . |

OTHER PUBLICATIONS

Pursel et al., 1989, "Genetic Engineering of Livestock," *Science* 244:1281–1288.

Wilmut et al., 1988, "A revolution in animal reading," *New Scientist* pp. 56–59.

Aboussekhra et al. 1992, Semidominant Suppressors of Srs2 Helicase Mutations of *Saccharomyces cerevisiae* Map in the RAD51 Gene, Whose Sequence Predicts a Protein with Similarities to Procaryotic RecA Proteins, Mol. Cell. Biol. 12:3224–3234.

Adra et al., 1987, "Cloning and expression of the mouse pgk–1 gene and the nucleotide sequence of its promoter", Gene 60:65–74.

Ashley et al., 1995, "Dynamic changes in Rad51 distribution on chromatin during meiosis in male and female vertebrates" Chromosoma 104:19–28.

Basile et al., 1992, "Nucleotide Sequence and Transcriptional Regulation of the Yeast Recombinational Repair Gene RAD51", Mol. Cell. Biol. 12:3235–3246.

Benson et al., 1994, "Purification and characterization of the human Rad51 protein, an analogue of *E.coli* RecA", EMBO 13:5764–5771.

Bezzubova et al., 1993, "A chicken RAD51 homologue is expressed at high levels in lymphoid and reproductive organs", Nucl. Acids Res. 21:1577–1580.

Bishop, 1994, "RecA Homologs Dmc1 and Rad51 Interact to Form Multiple Nuclear Complexes Prior to Meiotic Chromosome Synapsis", Cell 79:1081–1092.

Blochlinger et al., 1984, "Hygromycin B Phosphotransferase as a Selectable Marker for DNA Transfer Experiments with Higher Eucaryotic Cells", Mol. Cell. Biol. 4:2929–2931.

Bradley, 1987, In "Teratocarcinomas and embryonic stem cells: a practical approach", E. Robertson, ed. (Oxford: IRL Press), pp. 113–151.

Broder et al., 1990, "Antiretroviral Therapy in AIDS", Ann. Int. Med. 113:604–618.

Campisi, 1996, "Replicative Senescence: An Old Lives' Tale?", Cell 84:497–500.

Ch'ng et al., 1989, "Antisense RNA complementary to 3' coding and noncoding sequences of creatine kinase is a potent inhibitor of translation in vivo", Proc. Natl. Acad. Sci. USA 86:10006–10010.

Choulika et al., 1995, "Induction of Homologous Recombination in Mammalian Chromosomes by Using the I–Scel System of *Saccharomyces cerevisiae*", Mol. Cell. Bio. 15:1968–1973.

Cleaver, 1994, "It Was a Very Good Year for DNA Repair", Cell 76:1–4.

Donehower et al., 1992, "Mice deficient for p53 are developmentally normal but susceptible to spontaneous tumours", Nature 356:215–221.

Evans et al., 1981, "Establishment in culture of pluripotential cells from mouse embryos", Nature 292: 154–156.

Game, 1983, Radiation–sensitive mutants and DNA repair in yeast. p. 109–137. In: "Yeast genetics: fundamental and applied aspects." J.F.T. Spencer, D. Spencer, and A.R.W. Smith (eds.), Springler–Verlag, New York.

Gavrieli et al., 1992, "Identification of Programmed Cell Death In Situ via Specific Labeling of Nuclear DNA Fragmentation", J. Cell. Bio. 119:493–501.

Goldstein et al., 1975, "X–Ray Sensitivity of the Preimplantation Mouse Embryo in Vitro", Rad. Res. 62:276–287.

Gough et al., 1989, "LIF: a Molecule with Divergent Actions on Myeloid Leukaemic Cells and Embryonic Stem Cells", Reprod. Fertil. Dev. 1:281–288.

Graham et al., 1993, "Even–numbered rhombomeres control the apoptotic elimination of neural crest cells from odd–numbered rhombomeres in the chick hindbrain", Devel. 119:233–245.

(List continued on next page.)

*Primary Examiner*—Jasemine C. Chambers
*Assistant Examiner*—Jill D. Martin
*Attorney, Agent, or Firm*—Pennie & Edmonds LLP

[57] ABSTRACT

The present invention discloses MmRad51-deficient transgenic mice and mouse cells, as well as MmRad51/p53-deficient transgenic mice and mouse cells. Also described is a method of screening for proteins that rescue the senescence phenotype in MmRad51/p53-deficient cells.

23 Claims, 8 Drawing Sheets

OTHER PUBLICATIONS

Haaf et al., 1995, "Nuclear foci of mammalian Rad51 recombination protein in somatic cells after DNA damage and its localization in synaptonemal complexes" Proc. Natl. Acad. Sci., USA 92:2298–2302.

Haber, 1992, "Mating–type gene switching in *Saccharomyces cerevisiae*", Trends Genet. 8:446–452.

Helene., C. and Toulme, J., 1990, "Specific regulation of gene expression by antisense, sense and antigene nucleic acids", Biochimica et Bioshys. Acta 1049:99–125.

Hogan et al., 1994, Manipulation of the mouse embryo: A laboratory manual. 2nd ed. Cold Spring Harbor Press. pp. 265–272.

Jang et al., 1994, "Cloning and sequence analysis of rhp51+, a *Schizosaccharomyces pombe* homolog of the *Saccharomyces cerevisiae* RAD51 gene", Gene 142:207–211.

Kaufman, 1992, The atlas of mouse development, Academic Press, pp. 20–37.

Ko and Prives, 1996, "p53: puzzle and paradigm", Genes & Dev. 10:1054–1072.

Krasin and Hutchinson, 1977, "Repair of DNA Double–strand Breaks in *Escherichia coli*, which Requires recA Function and the Presence of a Duplicate Genome", J. Mol. Biol. 116:81–98.

Krogstad and Champoux, 1990, "Sequence–Specific Binding of DNA by the Moloney Murine Leukemia Virus Integrase Protein", J. Virol. 64:2796–2801.

Loreau et al., 1990, "Blockage of AMV reverse transcriptase by antisense oligodeoxynucleotides", FEBS Letters 274:53–56.

Mansour et al., 1988, "Disruption of the proto–oncogene int–2 in mouse embryo–derived stem cells: a general strategy for targeting mutations to non–selectable genes", Nature 336:348–352.

Mielke, et al., 1995, "A simple assay for puromycin N–acetyltransferase: selectable marker and reporter", Trend. Genet. 11:258–259.

Morita et al., 1993, "A mouse homolog of the *Escherichia coli* recA and *Saccharomyces cerevisiae* RAD51 genes", Proc. Natl. Acad. Sci., USA, 90:6577–6580.

Mortimer, 1958, "Radiobiological and Genetic Studies on a Polyploid Series (Haploid to Hexaploid) of *Saccharomyces cerevisiae*", Radiat. Res. 9:312–326.

Munir et al., 1990, "Antisense RNA Production in Transgenic Mice", Somat. Cell Mol. Genet. 16:383–394.

Muris et al., 1993, "Cloning the RAD51 homologue of *Schizosaccharomyces pombe*", Nucleic Acids Res. 21:4586–4591.

Ogawa et al., 1993, "Similarity of the Yeast RAD51 Filament to the Bacterial RecA Filament", Science 259:1896–1899.

Pepin et al., 1991, "Impaired type II glucocoritcoid–receptor function in mice bearing antisense RNA transgene", Nature 355:725–728.

Petes et al., 1991, Recombination in yeast, In: The Molecular and Cellular Biology of the Yeast Saccharomyces, pp. 407–521, J.R. Broach, J.R. Pringle, and E.W. Jones (eds.), Cold Spring Harbor Laboratory Press, Cold Spring Harbor, New York.

Pfarr et al., 1986, "Differential Effects of Polyadenylation Regions on Gene Expression in Mammalian Cells", DNA 5:115–122.

Radding, 1991, "Helical Interactions in Homologous Pairing and Strand Exchange Driven by RecA Protein", J. Biol. Chem. 266:5355–5358.

Robertson, 1987, In "Teratocarcinomas and embryonic stem cells: a practical approach", E. J. Robertson, ed. (Oxford: IRL Press), pp. 71–112.

Rockmill et al., 1995, "Roles for two RecA homologs in promoting meiotic chromosome synapsis", Genes & Devel. 9:2684–2695.

Roth et al., 1995, "How to make ends meet", Current Biology 5:496–499.

Rouet et al., 1994, "Introduction to Double–Strand Breaks into the Genome of Mouse Cells by Expression of a Rare–Cutting Endonuclease", Mol. Cell. Bio. 14:8096–8106.

Shinohara et al., 1992, "Rad51 Protein Involved in Repair and Recombination in *S. cerevisiae* Is a RecA–like Protein", Cell 69:457–470.

Shinohara et al., 1993, "Cloning of human, mouse and fission yeast recombination genes homologous to RAD51 and recA", Nature Genet. 4:239–243.

Stout, J. and Caskey, T., 1990, "Antisense RNA Inhibition of HPRT Synthesis", Somat. Cell Mol. Genet. 16:369–382.

Sung, 1994, "Catalysis of ATP–Dependent Homologous DNA Pairing and Strand Exchange by Yeast RAD51 Protein", Science 265:1241–1243.

Sung and Robberson, 1995, "DNA Strand Exchange Mediated by a RAD51–ssDNA Nucleoprotein Filament with Polarity Opposite to That of RecA", Cell 82:453–461.

Terasawa et al., 1995, "Localization of RecA–like recombination proteins on chromosomes of the lily at various meiotic stages", Genes & Dev. 9:925–934.

von Melcher et al., 1992, "Selective disruption of genes expressed in totipotent embryonal stem cells", Genes and Development 6:919–927.

Yamamori et al., 1989, "The Cholinergic Neuronal Differentiation Factor from Heart Cells Is Identical to Leukemia Inhibitory Factor", Science, 246:1412–1416.

Yoshimura et al., 1993, "Cloning and sequence of the human RecA–like gene cDNA", Nucleic Acids Res. 21:1665.

Bradley et al., Biotechnology, vol. 10, pp. 534–539, 1992.

Capecchi, Scientific American, vol. 270, pp. 34–41, Mar. 1994.

Sturzbecher et al., EMBO Journal, vol. 15. pp. 1992–2002, Apr. 15, 1996.

FIG. 4A Control
FIG. 4B Mutant
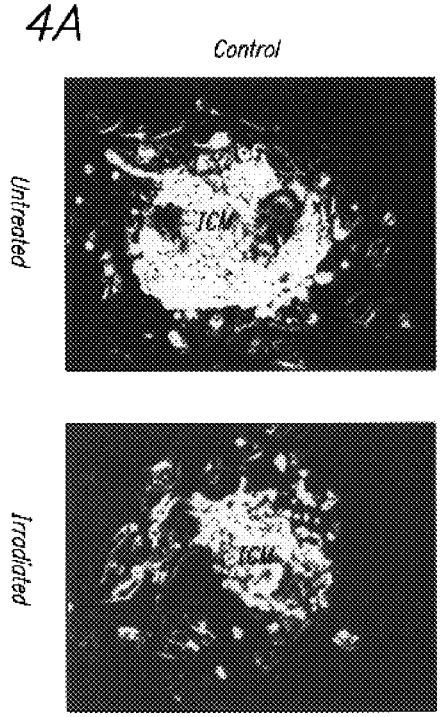
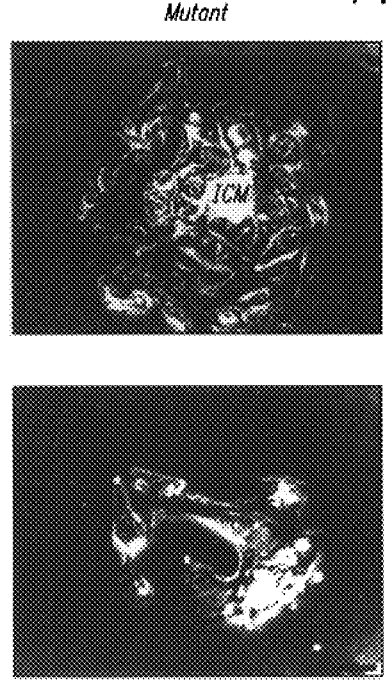
FIG. 4C
FIG. 4D

FIG. 6A
Control
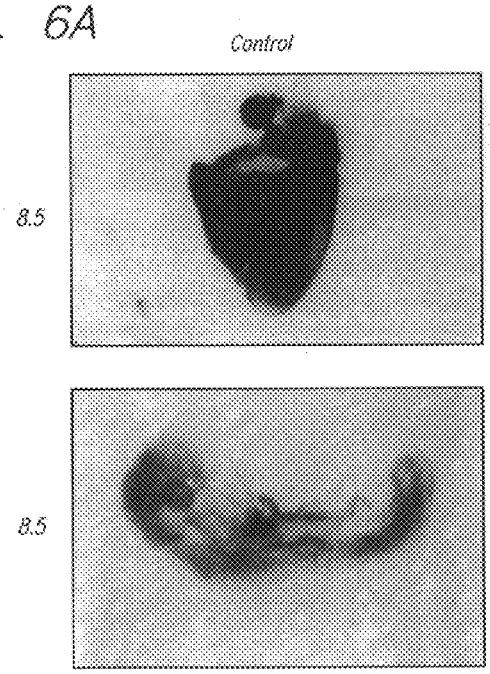
FIG. 6B
Double Mutant
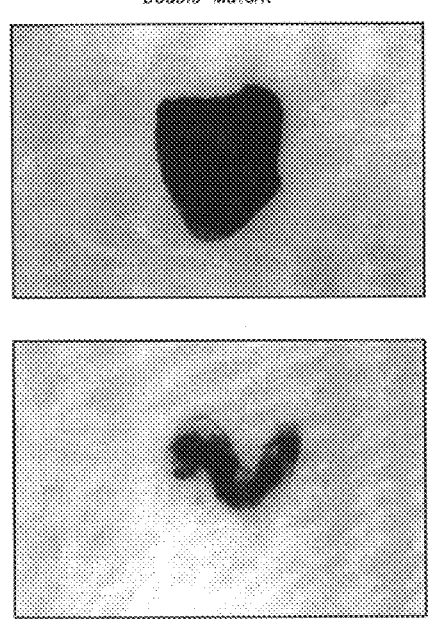
FIG. 6C
FIG. 6D

MMRAD51-DEFICIENT CELLS AND TRANSGENIC MICE

1.0. FIELD OF INVENTION

The present invention relates to MmRad51-deficient cells and nonhuman transgenic animals. The MmRad51-deficient cells and animals enable the identification of proteins, or altered forms thereof, that interact with MmRad51, or any other proteins in the MmRad51 DNA repair pathway.

2.0. BACKGROUND OF THE INVENTION

DNA repair and recombination are required by organisms to prevent the accumulation of mutations and to maintain the integrity of chromosomally encoded genetic information. Compromised genetic information is often associated with cell cycle arrest, programmed cell death, or cell senescence. Compromised genetic information has also been linked to cell cycle aberrations that are often associated with uncontrolled cell growth and possibly tumor formation.

Enzymes capable of repairing double-strand breaks (DSB) in DNA perform an essential function found in nearly all living cells. DSB repair may occur in conjunction with general DNA repair, or in a species-specific manner such as the mating-type switch in *Saccharomyces cerevisiae* and V(D)J (Variable [Diversity] Joining) recombination in mammals (reviewed by Friedberg et al., 1991; Haber, 1992, Trends Genet. 8:446–452; Roth et al., 1995, Current Biology 5:496–499). In bacteria and yeast cells, DSB are predominately repaired by a homologous recombination pathway (Mortimer, 1958, Radiat. Res. 9:312–316; Krasin and Hutchinson, 1977, J. Mol. Biol. 116:81–98). However, in mammalian cells, DSB may be repaired by either a homologous or a nonhomologous recombination pathway (Rouet et al., 1994, Mol. Cell. Bio. 14:8096–8106; Choulika et al., 1995, Mol. Cell. Bio. 15:1968–1973).

In the budding yeast, *S. cerevisiae*, repair of DSB occurs through a homologous recombination pathway that depends on the RAD52 epistasis group (Rad50–Rad57), which was identified in cells sensitive to ionizing radiation. Some members of this group were shown to be important for recombinational repair during mitotic and meiotic recombination (for reviews see Game, 1983, Radiation-sensitive mutants and DNA repair in yeast. p. 109–137. In: "Yeast genetics: fundamental and applied aspects." J. F. T. Spencer, D. Spencer, and A. R. W. Smith (eds.), Springler-Verlag, New York; Petes et al., 1991, Recombination in yeast, In: The Molecular and Cellular Biology of the Yeast Saccharomyces, pp. 407–521, J. R. Broach, J. R. Pringle, and E. W. Jones (eds.), Cold Spring Harbor Laboratory Press, Cold Spring Harbor, N.Y.). Among the members of the RAD52 epistasis group, ScRad51 is interesting because of its similarity to the *Escherichia coli* recombination protein, RecA (Shinohara et al., 1992, Cell 69:457–470; Aboussekhra et al. 1992, Mol. Cell. Biol. 12:3224–3234; Basile et al., 1992, Mol. Cell. Biol. 12:3235–3246). Both enzymes share approximately 30 percent homology over a region of about 220 amino acids and polymerize on double-stranded and single-stranded DNA (dsDNA, ssDNA), showing a nearly identical helical filament (Ogawa et al., 1993, Science 259:1896–1899; Sung and Robberson, 1995, Cell 82:453–461). ScRad51 and RecA catalyze an ATP-dependent strand exchange between homologous DNA molecules (Sung, 1994, Science 265:1241–1243; Sung and Robberson, 1995; for review see Radding, 1991, J. Biol. Chem. 266:5355–5358).

ScRad51 repairs DSB by recombination, and DSB accumulate at recombination hot spots in cells that lack ScRad51 during meiosis (Shinohara et al., 1992). ScRad51 and another RecA homologue, DMC1, colocalized to meiotic nuclei (Bishop, 1994, Cell 79:1081–1092) and promoted meiotic chromosome-synapsis (Rockmill et al., 1995, Genes & Devel. 9:2684–2695). Therefore, ScRad51 may mediate meiotic recombination by binding to single strands generated at DSB which could lead to pairing and strand exchange during meiosis as suggested by Sung and Robberson, 1995.

RecA/ScRad51 homologues have been discovered in a wide range of organisms including the fission yeast Schizosaccharomyces pombe (Shinohara et al., 1993, Nature Genet. 4:239–243; Muris et al., 1993, Nucleic Acids Res. 21:4586–4591; Jang et al., 1994, Gene 142:207–211), lilies (Terasawa et al., 1995, Genes & Dev. 9:925–934), chicken (Bezzubova et al., 1993, Nucl. Acids Res. 21:1577–1580), mouse (Shinohara et al., 1993; Morita et al., 1993, Proc. Natl. Acad. Sci., U.S.A., 90:6577–6580) and human (Shinohara et al., 1993; Yoshimura et al., 1993, Nucleic Acids Res. 21:1665). RecA/ScRad51 homologues also appear to be involved in DNA repair, and recombination as based on the following indirect evidence: 1) Conserved RecA homology—MmRad51 is 83% homologous and 69% identical to ScRad51, and 51% homologous and 28% identical to RecA (Shinohara et al., Morita et al., 1993). Shared homology between mammalian and yeast Rad51 suggest conserved function due to the remarkable similarity between other mammalian and yeast repair pathways (reviewed by Cleaver, 1994, Cell 76:1–4); 2) Expression pattern: MmRAD51 is highly expressed in tissues involved in meiotic recombination (testis and ovary; Shinohara et al., 1993; Morita et al., 1993) and expression of the *S. pombe* homologue, SpRAD51 (also called rhp51+), increased after cells were treated with methyl methanesulfonate suggesting a role in DNA repair (Jang et al., 1994); 3) Protein cellular localization: Mouse, chicken, and lily Rad51 localized as discrete foci on meiotic chromosomes at varying concentrations during prophase 1, possibly on the lateral elements and recombination nodules, suggesting a role in the repair of DSB during meiotic recombination (Haaf et al., 1995, Proc. Natl. Acad. Sci., U.S.A. 92:2298–2302; Ashley et al., 1995, Chromosoma 104: 19–28; Terasawa et al., 1995). Human Rad51, HsRad51, located to the nucleus with increasing concentration after exposure to DNA damaging agents suggesting a repair function (Haaf et al., 1995); 4) Filament formation on DNA: HsRad51 bound to ssDNA demonstrating a potential for strand exchange (Benson et al., 1994, EMBO 13:5764–5771). The present invention has provided the first direct evidence of the function of mammalian Rad51 and provides insight into recombinational repair in animal cells.

3.0. SUMMARY OF THE INVENTION

RecA in *Escherichia coli* and it's homologue, ScRad51 in *Saccharomyces cerevisiae*, are known to be essential for recombinational repair. The RecA/ScRad51 homologue in mammals (mice), MmRad51, was mutated to determine it's function, and the mutant embryos derived from MmRad51 cells arrested during early development. This arrest was accompanied by a decrease in cell proliferation, followed by programmed cell death and chromosome loss. Radiation sensitivity was also demonstrated in trophectoderm-derived cells.

Interestingly, embryonic development progressed further in a p53 null background even though fibroblasts derived from MmRad51/p53-deficient embryos failed to proliferate in tissue culture. The MmRad51-deficient and MmRad51/p53-deficient cells are useful for the identification of genes whose protein products rescue the senescence phenotype.

Accordingly, one object of the present invention is the engineering of animal cells, preferably mammalian, that are MmRad51-deficient due to the targeted disruption of the MmRad51 gene, and hence produce less than wild-type levels of MmRad51 activity.

Another embodiment of the present invention is the use of the MmRad51-deficient cells to produce non-human transgenic animals. Preferably, these transgenic animals shall breed true for the transgenic trait (genotype and/or phenotype). Accordingly, an additional object of the present invention is to provide non-human transgenic embryos or non-human transgenic animals, preferably mice, that are MmRad51-deficient.

Given that an MmRad51-deficiency may prove lethal in an otherwise wild-type genetic background, another object of the present invention is to provide animal cells that are both MmRad5l-deficient and p53-deficient. Thus, an additional embodiment of the present invention is a method of making transgenic non-human animals that comprise targeted gene disruptions that are normally lethal by introducing additional genetic engineering or mutations into the cells used to produce the transgenic animal.

Another object of the present invention is the use of MmRad51/p53 mutant cells to generate transgenic non-human animals or embryos, preferably rodent or murine, which are both MmRad51-deficient and p53-deficient. Accordingly, the present invention also contemplates transgenic non-human animals or embryos, preferably rodent or murine, which are both MmRad51-deficient and p53-deficient.

The MmRad51-deficient non-human transgenic animals of the present invention may be heterozygous or homozygous for the mutated MmRad51 allele.

4.0. BRIEF DESCRIPTION OF THE DRAWINGS

FIG. 1A–E. Genomic Structure and Targeting of MmRAD51. (A) Exons were labeled a–e because the 5' mRNA sequences were not located in this genomic fragment and the first exon was not known. A and B represent the Walker A- and B-type nucleotide-binding domains. Positive selection cassette, the box labeled +. Negative selection cassette, MCItk, the box labeled tk. All vectors were linearized using the KpnI (K) restriction site present in the polylinker. Exon a was used as a probe, and EcoRI (RI); EcoRV (RV); SacI (S) restriction sites are shown. Sense and antisense primers for RT-PCR, arrows were labeled as A and AS, respectively. Oligonucleotide probe for RT-PCR (*–) (B) Targeting with DVpuro (p). Upper panel, genomic DNA extracted from tails of mice. The wild-type (+/+) 15 kb EcoRV fragment was reduced to 10 kb (+/p). Lower panel, genomic DNA extracted from ES cells previously targeted with DVhygro (+/h). (C) Targeting with DVhygro (h). A 12 kb EcoRV fragment was produced (+/h). (D) Targeting with DVpuro2 into a cell line previously targeted with DVhygro. A 7 kb EcoRV fragment was produced. (E) RT-PCR analysis of day 7.0 embryos. Left panel, EtBr stained agarose gel. Right panel, autoradiogram after hybridization to oligonucleotide probe (*–). Controls (1–6, 9), and mutants (7, 8).

Figure 2A:
Figure 2B:
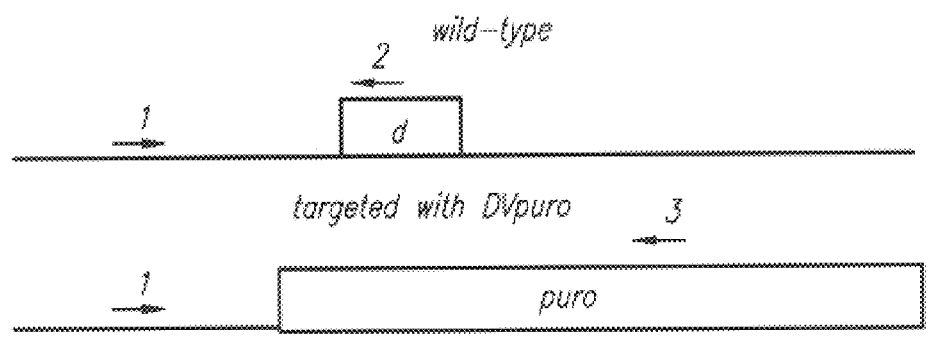
Figure 2C:
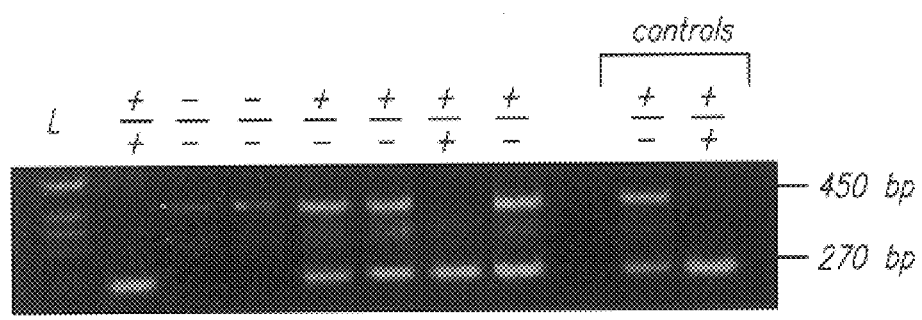

FIG. 2A–C. Day 7.5 control and rad51M1–/– embryos. (A) Wild-type, +/+; mutant, –/– (25× magnification). (B) Genotyping embryos by PCR. Sense primer (1) for wild-type and targeted copy. Antisense primer for wild-type copy (2) in exon d. Antisense primer for targeted copy (3) in pgk-1 promoter. Mutant band, 450 bp; wild-type band, 270 bp. (C) EtBr stained gel of the PCR reaction. Wild-type, +/+; mutant, –/–; heterozygote, +/–. DNA controls were extracted from rad51M1+/– and wild-type ES cells. The fragments were hybridized to an internal probe (not shown). A minor band is observed between the 450 and 270 bp bands; however, this band did not hybridize to the internal probe and disappeared at a higher annealing temperature.

FIG. 3A–H. Histological analysis of control and rad51M1–/– embryos. Control embryos (A, C, E, G), and mutant embryos (B, D, F, H) were used as indicated. Hematoxylin and eosin (H&E) stained day 7.5 embryos (A and B): ac, amniotic cavity; pcv, proamniotic cavity; ec, ectoplacental cone. Arrow points to epiblast. Hematoxylin-and eosin-stained day 6.5 embryos (C and D). BrdU labeling of day 5.5 embryos (E and F). TUNEL assay on day 7.5 embryos displayed in A and B (G and H). The epiblast region is shown, arrow in (A and B). Scale bar in (A–B), 120 μm; (C–D), 60 μm; (E–F), 30 μm; (G–H), 24 μm.

FIGS. 4A–B. Exposure of day 3.5 embryos to γ-radiation. Control embryos (A and C) and mutant embryos (B and D) are shown. No exposure (A and B) and 200 RADS exposure (C and D) are shown. Scale bar, 120 μm.

Figure 5A:
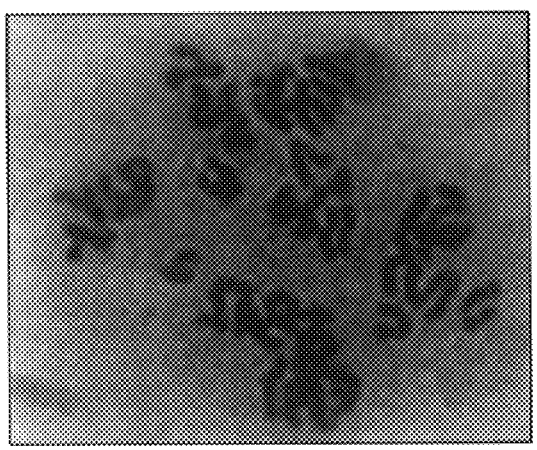
Figure 5B:
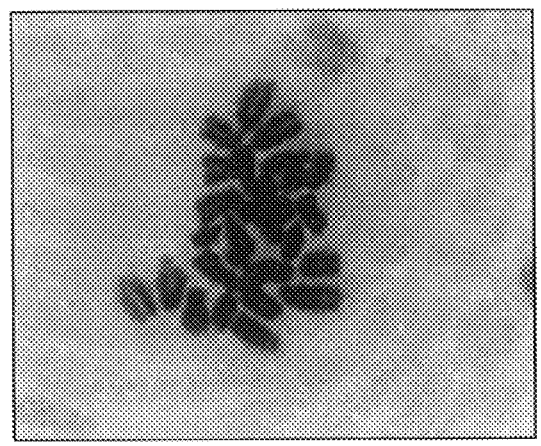

FIG. 5A–B. Metaphase spreads on cells derived from day 7.5 embryos. (A) Control, (B) mutant (1000× magnification).

FIG. 6A–D. Morphology of rad51M1–/– embryo in a p53–/– background. (A and C) Control (rad51M1+/–, p53+/–) and (B and D) double-mutant embryo. (A and B) Embryo in yolk sac. (C and D) Embryo removed from yolk sac. (12.5× magnification).

5.0. DETAILED DESCRIPTION OF THE INVENTION

The present invention is directed to the production of MmRad51-deficient cells, and MmRad51-deficient non-human animals. The non-human transgenic animals contemplated by the present invention generally include any vertebrates, and preferably mammals, which encode MmRad51, or a homolog of the MmRad51 gene. Such nonhuman transgenic animals may include, for example, transgenic pigs, transgenic rats, transgenic rabbits, transgenic cattle, transgenic goats, and other transgenic animal species, particularly mammalian species, known in the art. Additionally, bovine, ovine, and porcine species, other members of the rodent family, e.g. rat, as well as rabbit and guinea pig, and non-human primates, such as chimpanzee, may be used to practice the present invention. Particularly preferred animals are rats, rabbits, guinea pigs, and most preferably mice.

Preferred embodiments of the present invention include diploid non-human animal cells, animal embryos, and animals that contain two chromosomal alleles of the MmRad51 gene, wherein at least one of the MmRad51 alleles contains a mutation such that the cell produces less than wild-type levels of MmRad51 activity. Such MmRad51-deficient animals and cells are deemed to be useful as, inter alia, disease models for the analysis and testing of therapeutic agents, and the effects of mutagenic stimuli such as radiation and chemical mutagens.

The particularly preferred embodiments of the present invention have been specifically exemplified by the engineering of a diploid mouse cell containing two chromosomal alleles of the MmRad51 gene, wherein at least one of said alleles contains a mutation such said cell produces less than wild-type levels of MmRad51 activity.

Another embodiment of the present invention has been specifically exemplified by the construction of a mutant mouse embryo that produces less than wild-type levels of MmRad51 as a result of an engineered mutation in the MmRad51 gene.

Still another embodiment of the present invention has been exemplified by the engineering of a diploid mouse cell containing two chromosomal alleles of the MmRad51 gene and two chromosomal alleles of the p53 gene, where at least one allele at each locus has been mutated such that the cell produces less than wild-type levels of MmRad51 activity and p53 activity.

Yet another embodiment of the present invention has been exemplified by the generation of a mutant mouse embryo which produces less than wild-type levels of MmRad51 and p53 as a result of a mutation in the MmRad51 and p53 genes.

As discussed above, several embodiments the present invention have been shown to be operative as evidenced by the production of mouse cells, mouse embryos, and mice containing two chromosomal alleles of the MmRAD51 gene, wherein at least one of said alleles contains a mutation such that said cell produces less than wild-type levels of MmRad51 activity.

As used herein, MmRad51-deficient means that at least one of the two wild-type MmRad51 chromosomal alleles has been mutated such that less than wild-type levels of the MmRad51 activity are produced.

MmRad51 deficiency can be easily measured using by molecular biology, one can measure for a deficiency in MmRad51 messenger RNA levels by using reverse transcriptase polymerase chain reaction (RT-PCR) (see FIG. 1). For the purposes of the present disclosure, the term "MmRad51-deficient" includes both homozygous MmRad51 mutant cells, as well as cells that are heterozygous for the MmRad51 mutant genotype, although a homozygous genotype is preferable.

For the purposes of the present invention, a cell or animal that has been engineered to be MmRad51-deficient shall generally express at least about 20 percent less MmRad51 protein or activity than a corresponding wild-type cell or animal, and preferably at least about 50 percent less MmRad51 protein or activity than wild-type cells or animals, and more preferably at least about 90 percent less MmRad51 protein or activity than wild-type cells or animals. In a particularly preferred embodiment, the MmRad51-deficient cells or animals will produce less than 1.0 percent of the MmRad51 protein found in wild-type cells or animals, and in a specifically preferred embodiment the MmRad51 deficient cells or animals will produce undetectable levels of full-length (wild-type) MmRad51 transcript.

The mutation, or targeted disruption, in the target gene (e.g., MmRad51 or gene encoding p53) may be engineered using any of a number of well established mutations that are well known in the art. Preferably, the mutation shall be a deletion mutation, although substitution mutations and/or insertion mutations are included within the scope of the present invention.

Substitution mutations can be prepared by site directed mutagenesis that introduces a stop codon or other mutation near the 5' end of the target gene such that abortive production of MmRad51 protein results, or the production of a mutant protein which lacks MmRad51 activity.

Similarly, insertion mutations can be introduced within the MmRad51 gene taking advantage of the convenient restriction sites therein, such as any of the exonic restrictions sites or other sites which are easily identified by exonic sequencing of the MmRad51 gene and restriction mapping (FIG. 1).

Another method of introducing an insertion or other mutation consists of infecting with a retrovirus which integrates in the MmRad51 locus, thereby creating a mutated MmRad51 allele using methodologies similar to that described by von Melcher et al., 1992, Genes and Development 6:919–927.

An alternative method of isolating MmRad51-deficient cells is by the screening of ES cell libraries that have been treated to incorporate integrated viral (usually retrovirus or adeno-associated virus) sequences that inactivate the gene in which they have inserted. Once isolated, the MmRad51-deficient ES cell may be used to generate transgenic animals, or further mutated by the presently disclosed MmRad51 targeting vectors to generate a homozygous MmRad51 mutant cell or transgenic animal.

The mutants of the present invention preferably lack part of the DNA sequence coding for MmRad51 so that a defective MmRad51 allele is more likely to result. The coding region of the MmRad51 gene is approximately 1017 bp in size. Deletion mutants can be produced by eliminating a DNA fragment from a coding region of the MmRAD51 gene so that proper folding or substrate binding of the MmRad51 protein is prevented. The size of the deletion may vary, but in general a larger deletion is preferable to a smaller deletion since the larger deletions are more likely to result in a deficiency in MmRad51 activity.

Alternatively, by deleting a single base pair or two base pairs (or any number of base pairs not divisible by 3) from the coding region, one may generate frameshift mutations that alter the MmRad51 protein. In the latter instance, a truncated polypeptide may be produced because polypeptide synthesis is aborted due to a frame shift-induced stop codon. Still, changing a single base pair in the coding region of the MmRad51 gene could also be a mutation which, if resulting in an amino acid change, could alter the proper folding of the MmRad51 protein and thereby create an MmRad51-deficiency. A single amino acid change so generated could also alter the affinity of MmRad51 for its substrate and thereby result in a deficiency of MmRad51 activity.

Another alternative is to generate a deletion or other mutation in the non-coding region of the MmRad5 gene which effects the proper splicing of the MmRad51 messenger RNA. Such a mutation would effectively create a mutant MmRad51 transcript which is missing an entire exon or several exons normally present in the wild-type MmRad51 mRNA.

Another alternative is to delete a non-coding regulatory region to decrease expression of the MmRad51 gene. The preferred size of the deletion is about several hundred nucleotides near the 5' end of the gene. Preferably, such a deletion would eliminate a number of nucleotides from the coding region not evenly divisible by 3, thereby creating a frameshift mutation as well. Alternatively, promoter sequences may be deleted or altered that would diminish the transcription of the MmRad51 gene.

Antisense RNA transgenes may also be employed to partially or totally knock-out expression of specific genes (Helene., C. and Toulme, J., 1990, Biochimica Bioshys. Acta 1049:99; Pepin et al., 1991 Nature 355:725; Stout, J. and Caskey, T., 1990, Somat. Cell Mol. Genet. 16:369; Munir et al., 1990, Somat. Cell Mol. Genet. 16:383), each of which is herein incorporated by reference.

"Antisense polynucleotides" are polynucleotides that: (1) are complementary to all or part of a reference target sequence, such as the sequence of the MmRad51 gene, and specifically hybridize to a complementary target sequence, such as a chromosomal gene locus mRNA. Such complementary antisense polynucleotides may include nucleotide substitutions, additions, deletions, or transpositions, so long as specific hybridization to the relevant target sequence is retained as a functional property of the polynucleotide. Complementary antisense polynucleotides include antisense RNA which can hybridize specifically to individual mRNA species and hinder or prevent transcription and/or RNA processing of the mRNA species and/or translation of the encoded polypeptide (Ching et al., 1989, Proc. Natl. Acad. Sci. U.S.A. 86:10006–10010; Broder et al., Ann. Int. Med. 113:604–618; Loreau et al., 1990, FEBS Letters 274:53–56; Holcenberg et al., WO91/11535; WO91/09865; WO91/04753; WO90/13641; and EP 386563, each of which is incorporated herein by reference). An antisense sequence is a polynucleotide sequence of at least about 15 contiguous nucleotides in length, typically at least 20 to 30 nucleotides in length, and preferably more than about 30 nucleotides in length that is substantially complementary to a target gene sequence, or sequences, in a cell. In some embodiments, antisense sequences may have substitutions, additions, or deletions as compared to the complementary target sequence but as long as specific hybridization is retained, the polynucleotide will generally function as an antisense inhibitor of gene expression.

For the purposes of the present invention, the antisense sequence is complementary to an endogenous MmRad51 target gene sequence. In some cases, sense sequences corresponding to the MmRad51 target region sequence may function to suppress expression, particularly by interfering with transcription. Alternatively, an antisense polynucleotide will generally suppress MmRad51 expression at a post transcriptional level.

Given that antisense polynucleotides inhibit the production of the polypeptide(s) in cells, they may further alter a non-human transgenic animal's capacity to produce MmRad51 protein.

Antisense polynucleotides may be produced from a heterologous expression cassette inserted into transgenic pluripotent embryonic stem cells which may subsequently be used to generate the presently described MmRad51-deficient animals. Where the expression of the antisense polynucleotide is placed under the control of promoter elements that are primarily, or exclusively, active under specific conditions or at specific phases of embryonic development, it is possible to selectively suppress expression of the target gene.

The gene modified animal cells of the present invention can be prepared by any of several techniques that are well established in the art. In particular, techniques conceptually similar to those taught in U.S. Pat. No. 5,464,764 issued to Capecchi and Thomas on Nov. 7, 1995, herein incorporated by reference, may be used. In general, MmRad51-defective cells may be engineered using the following steps:

(1) Constructing a targeting vector comprising a cloning vector and a DNA fragment containing at least one positively selectable marker gene (positive selection marker), flanked by two regions of the mouse MmRad51 gene or genomic locus which are in the same 5' to 3' orientation to one another referred to as the regions of homology;

(2) Including in the targeting vector a negatively selectable marker gene (negative selection marker) adjacent to one of the regions of homology. This negatively selectable marker may increase the likelihood of recovering the desired homologous recombination event deleting a portion of the MmRad51 gene but it is not required;

(3) Transfecting MmRad51$^{+/+}$ mouse cells with the targeting vector of step (2);

(4) Screening or selecting for said marker(s) in the resulting transfected mouse cells of step (3); and (5) Screening for MmRad51-deficient mouse cells from those cells in step (4) which are found to contain or express said positive selection marker(s) and not express said negative selection marker(s).

The precise MmRad51 gene or gene locus sequences which must be present in the targeting vector of step (1) will depend on the sequences chosen for the deletion, and (2) the restriction nucleases to be employed in the engineering of the deletion mutant.

The specific regions of homology required in step (1) depend on the specifics of the deletion in the targeting vector. In general, the size of the homology regions used in the targeting vector will be at least about 400 bp, though longer or shorter regions could be used. In general it is preferable to use homology regions of approximately 1.5 kb or greater to insure a high degree of targeting efficiency. The targeting vector described in detail in FIG. 1, the 5' and 3' homology regions on both sides of the deletion were about 3.5 kb.

The size of the deletion may also vary depending upon the type of homology regions used in the targeting vector. Where non-contiguous regions of homology are used in the targeting vector, the region normally located between the regions of homology in the wild-type allele will be deleted after homologous recombination with the targeting vector. The region to be deleted in the present invention is approximately 1.7 kb in length although more or less sequence could have been deleted while providing the desired MmRad51-deficiency. Preferably, the deletion shall include at least one exon or a portion of an exon of the MmRad51 gene so as to result in mutant MmRad51 messenger RNA.

The particular positive and negative selection markers employed in the present invention are not critical to the practice of the invention. Examples of preferred positive and negative selection markers are listed in Table I of U.S. Pat. No. 5,464,764. The positive selectable marker should be located between the regions of homology and the negative marker, if one is used, should be outside the regions of homology, either 5' or 3' to those regions as shown in FIG. 1a. The regions of homology should generally be present in the vector in the same 5' to 3' orientation relative to one another. Conversely, the relative orientations of the positive and negative selectable markers are not critical. In fact, it is not really necessary to include a negative selectable marker, even though the presence of the negative marker may improve selection for targeted clones.

Preferably, the positive selectable marker is expressed in the cells that are targeted for gene modification. Positive and/or negative selection markers are deemed to be functional in the transfected cells if the DNA sequences encoding the selectable markers are capable of conferring either a positive or negative phenotypic selection characteristic to cells expressing the sequences. In general, the marker will be operably linked to a regulatory sequence that mediates the expression of the marker. A nucleic acid marker is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous.

Additionally, the means by which the positive selectable marker gene is made functional is not critical to the present invention. Positive selection is accomplished by exposing the cells to an appropriate agent which kills or otherwise selects against cells that do not contain or express an integrated positive selection marker. A representative, but not limiting, list of such agents is presented in Table I. The positive selectable marker gene may have a promoter driving its expression or it may be driven by the juxtaposition of transcriptional elements at the target locus with the positive selectable marker. The latter gene organization requires that the transcriptional elements are active in the transfected cells.

In addition to a positive selection marker, the mutation engineered into the targeting vector may contain DNA sequence, e.g., an oligonucleotide linker, in place of the deleted MmRad51 DNA. The oligonucleotide linker is generally 8–10 nucleotides in length, but can be longer, e.g. about 50 nucleotides, or shorter, e.g. 4, 5 or 7 nucleotides. The preferred length of the oligonucleotide linker is about 20 to 40 nucleotides in length. The DNA sequence of the oligonucleotide linker is not critical.

The method of inserting the oligonucleotide between the regions of homology in the targeting vector DNA will depend upon the type of oligonucleotide linker used. Palindromic double stranded linkers containing one or more restriction nuclease sites in the oligonucleotide sequence (New England Biolabs) may be inserted by well known procedures (Maniatis et al., 1982, Molecular Cloning, Cold Spring Harbor Laboratory, Cold Spring Harbor Press, New York)

Oligonucleotide linkers may also be inserted into deletions in plasmid DNA by tailing ends with complementary homopolymers using terminal transferase (Maniatis et al., supra), or a single stranded oligonucleotide linker may be inserted into a deletion in a plasmid by bridging, through annealing of an oligonucleotide containing ends complementary, to a cleaved plasmid's 3'-recessed and 3'-protruding cohesive ends, followed by filling-in the gap complementary to the oligonucleotide sequence with DNA polymerase (Klenow fragment). After subsequent ligation with T4 DNA ligase, closed circular DNA molecules can be regenerated. If the targeting vector is designed such that the deleted region interrupts an exon, the judicious choice of oligonucleotide linker length and sequence, may also produce frame shift mutations and/or stop codons may be produced in the target gene to augment the effect of deletion within the mouse MmRad51 gene.

Alternatively, site-directed mutagenesis may be used to simultaneously construct a specific deletion and insert a linker sequence by using a single stranded oligonucleotide to "loop-out" the desired region of the target gene (Krogstad and Champoux (1990) J. Virol. 64(6):2796–2801, herein incorporated by reference).

The mutation engineered in the targeting vector can contain DNA sequences between the regions of MmRad51 gene homology in addition to the positive selection marker, for example, splice acceptor sequences. Such sequences have been shown to facilitate aberrant splicing to create mutant message.

The DNA used in the regions of homology should be derived from genomic DNA from the MmRad51 gene locus, or sequences that flank the MmRad51 gene locus. Where the mouse gene is targeted, the strain of mouse from which the DNA is derived is not important but it should preferably be the same as the strain of mouse as the cells targeted for gene transfer. Using DNA in the homology regions that is isogenic to the cells in which gene targeting will be performed may enhance the efficiency with which gene targeting is accomplished. The regions of homology may be derived from genomic libraries of mouse DNA which may be cloned into a variety of library vectors such as lambda phage vectors, cosmid vectors, plasmid vectors, p1 phage vectors, yeast artificial chromosome vectors, or other vectors. Regions of homology to be used in the targeting vector may also be derived directly from genomic DNA using the polymerase chain reaction (PCR). This method relies on having some knowledge of the sequence of the MmRad51 gene which is published, or the flanking sequences. Regions of homology so derived could be subcloned directly into the targeting vector.

The particular cloning vector used to construct the described targeting vector shall generally contain, inter alia, two regions of MmRad51 homology separated by a positive selectable marker gene. Optionally, a negative selectable marker may also included in the either, or both regions flanking the regions of homology. In any event, the particular cloning vector used is not critical as long as it contains a gene coding for a selective trait, e.g. drug resistance. Examples of suitable cloning vectors include, but are not limited to, pBR322 and pBR322-based vectors (Sekiguchi, 1983), pMB9, pBR325, pKH47 (Bethesda Research Laboratories), pBR328, pHC79, phage Charon 28 (Bethesda Research Laboratories, Boehringer Mannheim Biochemicals), pKB11, pKSV-10 (P-L Biochemicals), pMAR420 (Otsuka, 1981) and oligonucleotide (dg)-tailed pBR322 (Bethesda Research Laboratories), pBluescript or similar plasmids (Stratagene), puc19 or similar plasmids (New England Biolabs).

Alternatively, a targeting vector comprising two regions of MmRad51 homology separated by a positive selectable marker gene and an optional flanking negative selectable marker could be cloned into other cloning vectors such as lambda phage vectors, cosmid vectors, plasmid vectors, p1 phage vectors, yeast artificial chromosome vectors, or other vectors. Another option is to prepare the components of the targeting vector synthetically by PCR and simply ligating each component into its proper position by choosing restriction endonuclease sites for ligation which insured proper orientation of the homology regions relative to each other, and to insure that the positive selectable marker was located between the regions of homology. Once constructed, this "targeting cassette" may be placed into suitable vectors such as those described above, or placed into any of a wide variety of viral vectors (adenovirus, papilloma virus, retrovirus, adeno-associated virus, etc.).

Other cloning vectors containing unique cloning sites which are useful in the present invention can be determined upon evaluation of restriction nucleases other than KpnI and SacI for the 5' homology and EcoRI and XhoI for the 3' homology which were used for the vector called DVpuro in the present invention (see FIG. 1). Other restriction nucleases that may be employed to produce fragments containing the mouse MmRad51 gene are readily apparent from the mouse MmRad51 gene restriction map. These alternative restriction nucleases may be used in conjunction with suitable cloning vectors to practice the present invention. A specific example of such a construct, a targeting vector called Dvpuro2, is described in FIG. 1. Other regions of the MmRad51 gene were obtained from restriction digests for Dvpuro2 as shown in FIG. 1. EcoRI and SacI were used in the 5' region of homology, and a EcoRI and XhoI fragment was used as the 3' region of homology. In fact, many combinations of restriction endonucleases may be used to generate MmRad51 targeting vectors for mutating the MmRad51 gene. These regions of homology may be cloned into any of a large number of commercially available plasmids such as the pBluescript series (Stratagene), the puc series (New England Biolabs), or the pGEM series (Promega).

The specific host employed for growing the targeting vectors of the present invention is not critical. Examples of such hosts include E. coli K12 RR1 (Bolivar et al., 1977); E. coli K12 HB101 (ATCC No. 33694); E. coli MM21 (ATCC No. 336780); and E. coli DH1 (ATCC No. 33849). The preferred host in the present invention is DH5α (Life Technologies). Similarly, alternative vector/cloning systems may be employed such as targeting vectors which grow in E. coli or Saccharomyces cerevisiae, or both, or plasmid vectors which grow in B. subtilus (Ure et al., 1983, Methods in Enzymology "Recombinant DNA", vol. 101, Part C, Academic Press, New York).

The specific mouse cell that is mutated in the present invention is not critical, but is preferably a precursor pluripotent cell. The term precursor means that the pluripotent cell is a precursor of the desired transfected pluripotent cell which is prepared in accordance with the present invention. The pluripotent cell may be cultured in vivo to form a mutant mouse (Evans et al., 1981, Nature 292: 292–156). Examples of mouse cells that may be employed in the present invention include embryonic stem (ES) cells (preferably primary isolates of ES cells), such as AB1 or AB2.1. Primary isolates of ES cells may be obtained directly from embryos, such as described for the EK.CCE cell line or for ES cells in general.

The particular embryonic stem cell employed in the present invention is not critical. Examples of such embryonic stem cells are AB 2.1, an hprt$^-$ cell line, AB 1, an hprt$^+$ cell line. Other selectable markers such as those outlined in Table I may be used in other stem cell lines.

The ES cells are preferably cultured on stromal cells, e.g., STO cells and/or primary embryonic fibroblast cells as described by Robertson, 1987, In "Teratocarcinomas and embryonic stem cells: a practical approach", E. J. Robertson, ed. (Oxford: IRL Press), pp. 71–112. The stromal (and/or fibroblast) cells serve to reduce the clonal outgrowth of abnormal ES cells. In some cases it may be preferable to culture the ES cells in the presence of leukocyte inhibitory factor, though it is not critical (Gough et al., 1989, Reprod. Fertil. Dev. 1:281; Yamagouchi et al., 1989, Science, 246:1412).

In order to obtain the MmRad51-deficient mice of the present invention, the mutant embryonic stems cells are injected into mouse blastocysts as described by Bradley, 1987, In "Teratocarcinomas and embryonic stem cells: a practical approach", E. Robertson, ed. (Oxford: IRL Press), pp. 113–151.

The particular mouse blastocysts employed in the present invention are not critical. Examples of suitable blastocysts include, but are not limited to, those derived from C57BL6 mice, C57BL6Albino, Swiss outbred, CFLP, MFI or others.

Mice heterozygous for the Mmrad51 mutant allele generated in the injected blastocyst may be screened for mutations in the MmRad51 gene, e.g., by Southern blotting using DNA probes for said mutation (FIG. 1), or by PCR (FIG. 2). For example, in Example 4 below, Southern blots using a probe 5' to the mutated locus identified mice heterozygous for the engineered mutation by detecting the presence of an 10 kb mutant DNA fragment and a 15 kb DNA fragment in wild-type cells (FIG. 1A, B).

The mutant mice of the present invention may be intercrossed to obtain embryos homozygous for the mutation in the MmRad51 gene, and may also be crossed with other mice strains to transfer the MmRad51 mutation into the strains. For example, as described in Example 4 below, Southern blots using a probe 5' to the mutated locus identified mice homozygous for the engineered mutation by only detecting the presence of a 10 kb DNA fragment corresponding to the mutant MmRad51 gene.

The present invention teaches that a p53$^-$ genetic background may at least partially rescue the lethal consequences of the homozygous (MmRad51–/–) condition.

Accordingly, another embodiment of the present invention is a method of producing transgenic embryos and animals which comprise mutations or genetic backgrounds that are otherwise lethal. Examples of such genotypes include dominant negative mutations (i.e., mutations that are lethal when heterozygously present), or homozygous lethal mutations (i.e., mutations in the MmRad51 gene).

The demonstration that a mutation in the p53 gene can partially rescue the MmRad51–/– phenotype, indicates that factors involved in the p53, or other, regulatory cascade may further rescue the MmRad51–/– phenotype. Accordingly, another method of extending the life or development of a cell, embryo, or animal containing a normally lethal genotype that is contemplated by the present invention includes, but is not limited to, the administration of appropriate second messengers ($Ca^{2+}$, cAMP or analogues thereof, triphosphoinositol, diacylglycerol, etc.), cytokines, hormones (steroidal, steroid-like, peptide, epinephrine, norepinephrine, histamine, prostaglandins, etc.), or a mixture thereof, to the cells or animals.

Additional "rescue" mutations may also be identified by screening the ES cell mutant library described above for the mutant genetic backgrounds that extend the viability of MmRad51–/– cells.

Another approach to extending the life of MmRad51–/– cells, embryos, and animals is to place an additional copy of the MmRad51 gene into the cells that is under the control of a promoter that is mainly or exclusively active during a specific period of the embryonic development, or may be modulated, induced, or suppressed by an external factor.

Using such a method, one may tightly control the expression of MmRad51 and study the effects MmRad51 null mutations "at will".

The examples below are provided solely to illustrate the subject invention. Given the level of skill in the art, one may be expected to modify any of the above or following disclosure to produce insubstantial differences from the specifically described features of the present invention. As such, the following examples are provided by way of illustration and are not included for the purpose of limiting the invention in any way whatsoever.

6.0. EXAMPLES

6.1. Cloning of the Mouse MmRad51 Gene

The mouse homologue of the *Saccharomyces cerevisiae* ScRad51 gene was cloned from a mouse 129-strain genomic library. More specifically, a fragment of the MmRad51 gene was obtained using oligonucleotides based on sequence and reverse transcriptase polymerase chain reaction on RNA from mouse cells. The resulting fragment of the mouse gene was subcloned into a plasmid vector pBluescript SK+ (Stratagene). A radiolabeled probe was made using this subclone of the MmRad51 gene, and used to screen a mouse 129-strain genomic lambda phage library to identify phage containing the homologous mouse gene. Three positive phage were isolated, grown, and DNA inserts were restriction mapped to produce a map of the MmRad51 genomic locus (see FIG. 1a). Based on restriction map data, putative exons were identified by hybridization and selected exonic sequencing was performed.

The sequence data for the cloned mouse MmRad51 gene revealed that it has substantial sequence similarity to the *S. cerevisiae* ScRad51 gene. That is, 69% identity was found at the amino acid level (Shinohara et al., 1993).

6.2. Construction of Targeting Vector

To generate MmRad51 -deficient mice, a targeting vector was constructed. This vector contains 3.5 kb of DNA homologous to the 5' region of the mouse MmRad51 gene, and 3.5 kb of DNA homologous to a region further downstream to the 5' region of homology to the MmRad51 gene. This vector also contains a marker for positive selection (the puromycin cassette), and a marker for negative selection (the thymidine kinase gene; Mansour et al., 1988, Nature 336:348–352).

More specifically, using the generated restriction map, a 5' homology region was selected and a homology region further downstream was selected. The 5' homology region was located near the 5' end of the MmRad51 genomic locus, and was isolated by an KpnI and SacI digest (FIG. 1A) which released approximately a 3.5 kb DNA fragment.

The downstream homology region was isolated by a EcoRI and XhoI digest which produced a DNA fragment of approximately 3.5 kb (FIG. 1A). The positive selectable marker used was the puromycin cassette.

To prepare the positive selection targeting vector, a 1.7 kb genomic fragment from SacI to EcoRI and containing coding nucleotides 413–530 was removed and replaced with the positive selectable marker. To prepare a positive-negative selection targeting vector, the negatively selectable tk gene was added exterior to the 3' homology region. The unique KpnI site was used to cut the vector prior to transfection (FIG. 1).

6.3. Transfection of Mouse Embryonic Stem Cells

Homologous recombination of the targeting vector with the MmRad51 genomic locus was effected in mouse embryonic stem cells (See FIG. 1). More specifically, 10 μg of the positive-negative targeting vector described in section 6.2. above was transfected into 1×10⁷ AB1 mouse 129 strain embryonic stem cells, and the resulting cells were grown in puromycin selection media to select for those cells which were transfected with the targeting construct. Negative selection against the tk gene was also applied using the drug FIAU so as to enhance the selection for those cells which had undergone a homologous recombination event at the MmRad51 locus. Surviving colonies were screened by mini-Southern, as described by Ramirez-Solis using a fragment of DNA from the MmRad51 locus which was 5' to the region of homology of the targeting vector as probes so as to detect the double reciprocal homologous recombination event between the targeting vector and the MmRad51 locus in the chromosome of the ES cell. ES cell genomic DNA for the minisouthern analysis was digested with restriction enzyme EcoRV. The desired recombination event was detected using a 5' probe which revealed a mutant allele of 10 kb as compared to the wild-type allele of 15 kb. Many positive ES cells clones were identified as correct replacement events, with an approximate 1.7 kb genomic deletion. The targeting frequency was approximately 1 in 10.

6.4. Generation of MmRad51-deficient Mice

Two ES cell clones obtained in Example 3 above were injected into C57BL6 Albino host blastocysts as has been described (Bradley, 1987). Injected blastocysts were implanted into pseudopregnant females and chimeric offspring were born as demonstrated by the mixture of agouti and albino coat colors (agouti contribution from the ES cell line and albino from the wild-type host embryos). Chimeric male mice were mated to wild-type C57BL6 Albino females and agouti pups were born indicating successful germline transmission of the ES cell component of the chimeric mouse, resulting in C57BL6 Albino/129 hybrids (referred to as C567BL6/129 hybrids). At three weeks of age, the offspring from the chimeric crosses were screened for the mutant MmRad51 allele as described below.

Genomic DNA was isolated from the resulting mice, and 10 μg of the genomic DNA was digested with EcoRV, and subjected to Southern blot analysis using the 5' probe described above. Two ES cell clones transmitted the mutant allele through the germline having an approximate deletion of 1.7 kb of genomic sequence and eliminating 117 bp of coding sequence of the mouse MmRad51 gene. A male and female mouse were identified as heterozygous for the mutant allele.

The male and female mouse which were found to be heterozygous for the MmRad51 mutation were intercrossed. The chimeric mouse that had demonstrated germline transmission was also crossed with a wild-type 129 strain mouse, in order to place the mutant allele (rad51M1-) on the 129 strain background. Genomic DNA was isolated from the resulting mice, and 10 μg of the genomic DNA was digested with EcoRV, and subjected to Southern blot analysis, using the 5' MmRad51 probe as described above. A single 15 kb band indicated a homozygous wild-type animal (+/+) animal, a single 10 kb band indicated an animal homozygous for the targeted mutant allele (rad51M1/rad51M1 or rad51M1−/− or mutant). The presence of both bands indicated a heterozygous animal (rad51M1−/+ or rad51M1+/−).

Several mating pairs of rad51M1+/− mice were intercrossed to obtain rad51M1−/− mice. Of 150 offspring from intercrosses, no homozygous mutant mice were observed. This result indicated that MmRad51 is essential sometime during development, and that the homozygous condition for the MmRad51 allele is lethal absent further engineering.

6.5. The rad51M1 Mutation is Most Likely Null

Figure 1B:
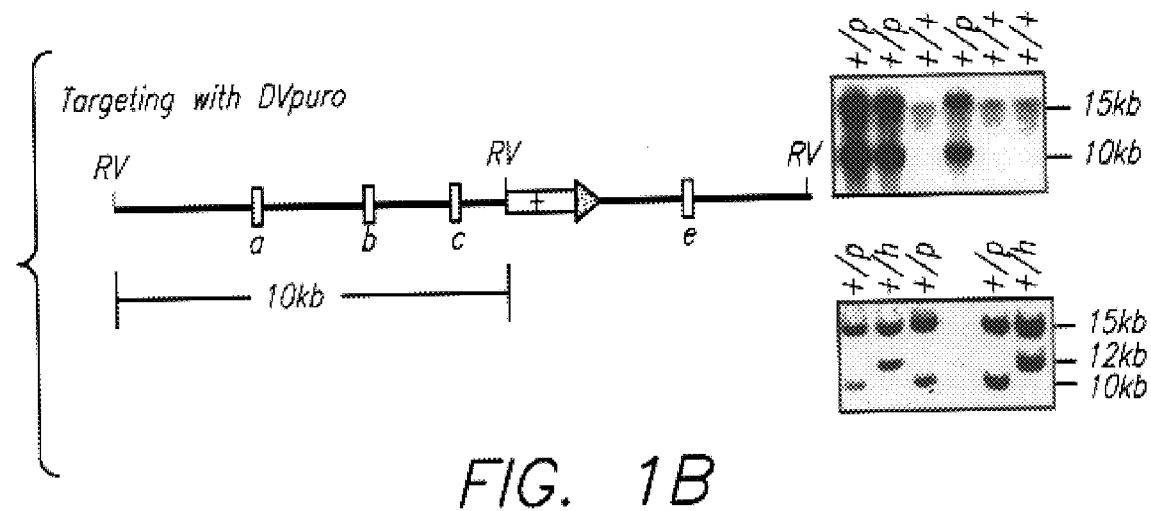
Figure 1C:
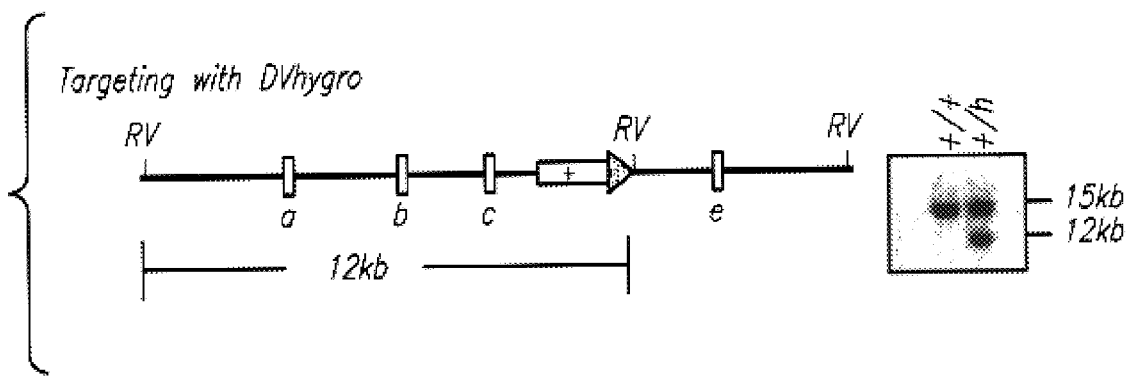
Figure 1D:
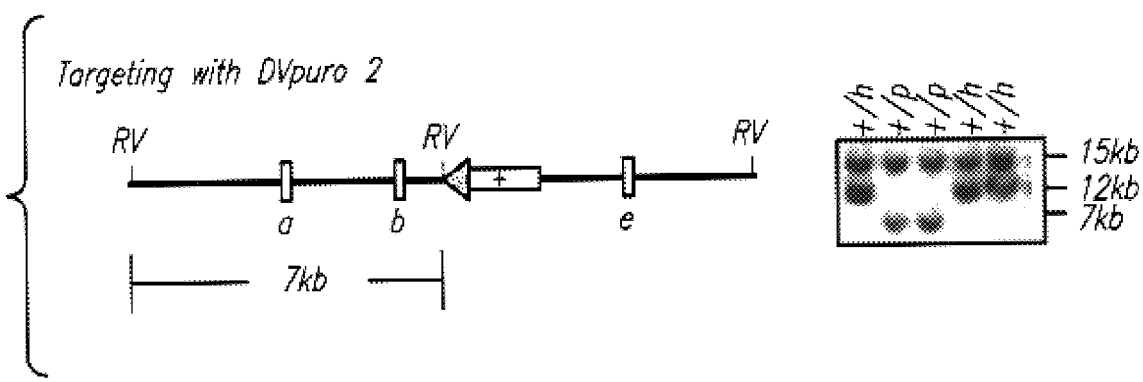
Figure 1E:
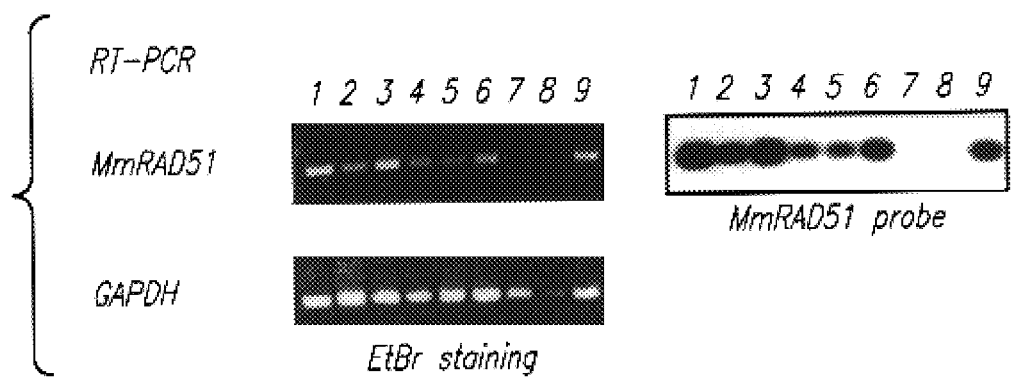

Consequences of the rad51M1 Mutation on MmRad51 transcript levels was determined by reverse transcriptase-polymerase chain reaction (RT-PCR) on mRNA isolated from control and mutant day 7.0 embryos (FIG. 1E). GAPDH and MmRad51 transcript levels were measured to control for mRNA loading and both transcripts were detected in control and mutant embryos. MmRad51 mRNA was detected in control but not mutant embryos, even after hybridization with an internal oligonucleotide probe. The out-of-frame deletion and the lack of MmRad51 mRNA make it likely that the rad51M1mutation was null, and that the null mutation was lethal in the homozygous condition.

6.6. Early Embryonic Lethal

Timed heterozygous matings were performed with rad51M1+/− females and rad51M1+/− males. The embryos were sacrificed 3.5–8.5 days later. Control (rad51M1+/−, rad51M1+/+), and rad51M1−/− embryos were the same gross size on days 3.5–6.0. However, by day 7.5, control embryos were much larger than mutant embryos which appeared to arrest development and growth 24–36 hours earlier (FIG. 2A). Some mutant embryos began to resorb into the placenta by day 7.5. The embryos were genotyped by PCR (FIGS. 2B and 2C).

Histological analysis was performed on day 5.5, 6.5 and 7.5 embryos (FIG. 3). After the histological analysis was complete, the sections were genotyped by PCR. rad51M1−/− embryos were hypocellular with abnormal cellular morphology; and transverse sections revealed that the cells were cuboidal in shape. Mutant embryos arrested at the early egg cylinder stage, typically observed by day 5.5 in control embryos. The proamniotic cavity was present in most control and mutant embryos by day 5.5; however, the amniotic cavity and mesoderm failed to develop in mutant embryos. The hypocellular condition and arrested development indicated reduced cell proliferation.

Figure 3A:
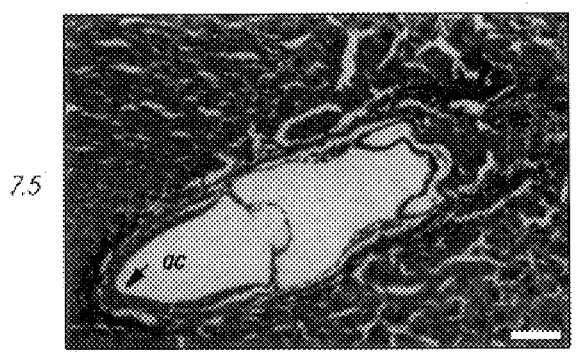
Figure 3B:
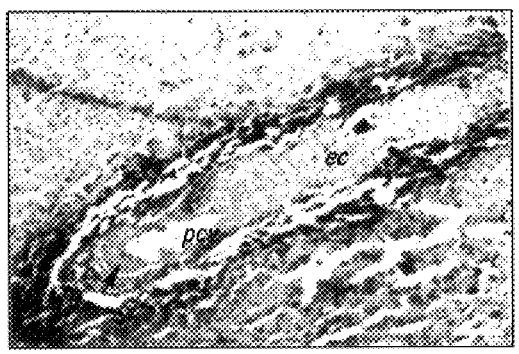
Figure 3C:
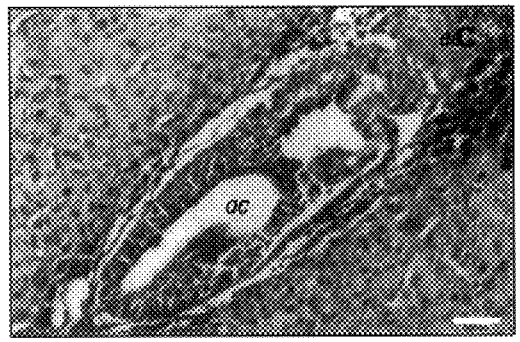
Figure 3D:
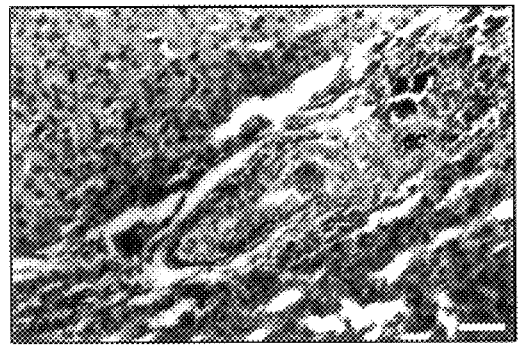
Figure 3E:
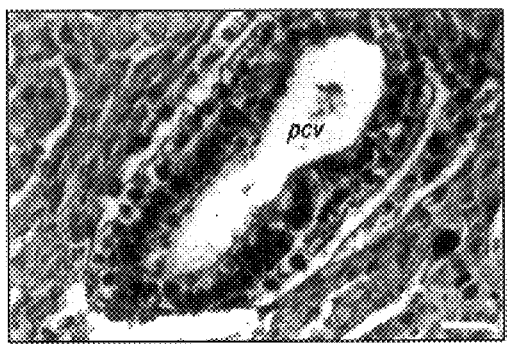
Figure 3F:
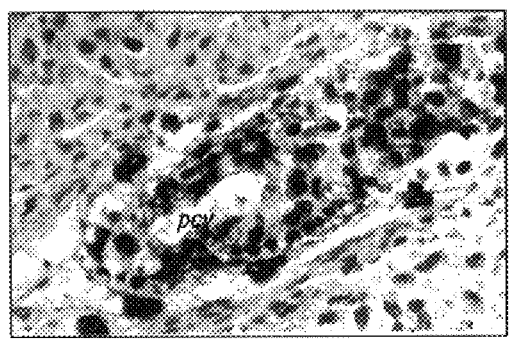

To observe cell proliferation, day 5.5, 6.5 and 7.5 embryos were labeled with BrdU (5-bromo-2'deoxyuridine). A lower percentage of cells incorporated BrdU in rad51M1−/− embryos as compared to control embryos indicating reduced proliferation or cell death (FIG. 3E, F). By day 5.5, 85% of the cells were labeled in control embryos compared to 50% of the cells in mutant embryos. By day 6.5, 100% of the cells were labeled in control embryos, compared to 85% in mutant embryos. By day 7.5, while control embryos still showed 100% of cells labeled, only 30–50% of cells were labeled in mutant embryos. A decrease in cell proliferation or induction of cell death may explain low incorporation levels in mutant embryos.

Figure 3G:
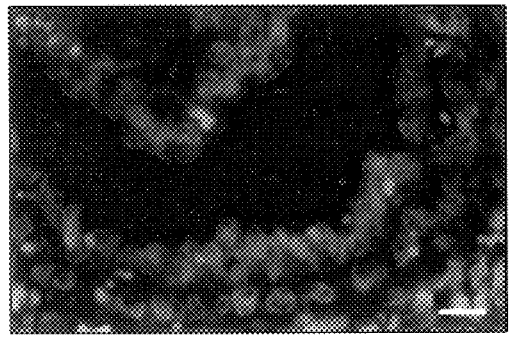
Figure 3H:
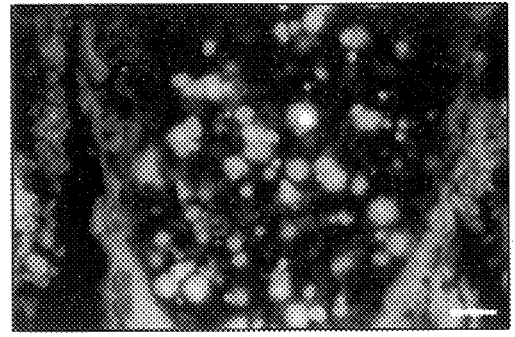

The time and extent of cell death was determined in mutant embryos. To observe nuclear fragmentation, one of the characteristic features of programmed cell death, a TUNEL assay (Gavrieli et al., 1992, J. Cell. Bio. 119:493–501) was performed on histological sections from day 6.5 and 7.5 embryos (FIG. 3G, H). Apoptotic cells were rarely observed in day 6.5 mutant and control embryos, and day 7.5 control embryos. However, apoptotic cells were common in the epiblast of day 7.5 mutant embryos. Therefore, reduced levels of BrdU incorporation in day 5.5 and 6.5 mutant embryos reflect a decrease in cell proliferation, while in day 7.5 embryos reflect decreased cell proliferation and increased cell death.

The rad51M1 mutation results in an early embryonic lethal in the homozygous condition. The mutant embryos arrested at the early egg cylinder stage. A decrease in cell proliferation was followed by programmed cell death.

5 6.7. rad51M1 Mutant Cells Fail to Proliferate

The effect of a homozygous rad51M1 mutation on cell viability was tested. Two approaches were used to generate rad51M1−/− cells. The first was to target both copies of MmRad51 in ES cells and the second was to derive mutant ES cells from cultured blastocysts.

We attempted to mutate both copies of MmRad51 in ES cells by sequential rounds of gene targeting. Three different vectors were used: Dvpuro, Dvpuro2, and Dvhygro (FIG. 1A). For positive selection, DVpuro and DVpuro2 contained a puromycin N-acetyltransferase cassette (Mielke, et al., 1995, Trend. Genet. 11:258–259) and DVhygro contained a hygromycin B phosphotransferase cassette (Blocklinger and Diggelmann, 1984, Mol. Cell. Biol. 4:2929–2931). All three vectors contained a negative selection cassette (MC1tk). The first MmRad51 copy was targeted with DVhygro which generated the same deletion as described for DVpuro (FIG. 1C). Two clones of ES cells, targeted with DVhygro, were transfected with DVpuro to target the remaining wild-type copy. However, all the clones retargeted the previously mutated copy (63 clones; FIG. 1B). One possible explanation for this observation is that the second vector favors retargeting the previously mutated allele because it shares greater homology with this allele than with the wild-type allele. Another explanation is that ES cells fail to proliferate when both copies of MmRad51 were targeted.

DVpuro shares 0.785 kb greater homology with the mutated allele as compared to the wild-type allele because the positive selection cassette in both DVpuro and DVhygro contain a common promoter (pgk-1; Adra et al., 1987, Gene 60:65–74) and polyadenylation signal (bovine growth hormone; Pfarr et al., 1986, DNA 5:115–122). A second vector, DVpuro2, was used to target the remaining wild-type copy of MmRad51. DVpuro2 did not contain greater contiguous homology to the DVhygro targeted allele because the positive selection cassette was in the opposite orientation and a larger deletion was present (FIG. 1A). Southern analysis demonstrated that DVpuro2 always retargeted the previously mutated allele (eight clones; FIG. 1D). These data indicate that the otherwise unmodified ES cells may not proliferate when both alleles of MmRad51 locus are mutant.

Cell proliferation and viability was tested with rad51M1−/− blastocysts grown in tissue culture. Blastocysts are composed of two cell types, pluripotent cells in the inner cellular mass and trophectoderm cells (reviewed by Kaufman, 1992, The atlas of mouse development, Academic Press, pp. 20–37; Hogan et al., 1994, Manipulation of the mouse embryo: A laboratory manual. 2nd ed. Cold Spring Harbor Press. pp. 265–272). When control blastocysts were grown in tissue culture, cells derived from the inner cellular mass became highly proliferative and cells derived from the trophectoderm (trophoblast-like cells) became relatively quiescent. rad51M1+/− mice were crossed and blastocysts recovered 3.5 days later. Blastocysts were grown in tissue culture to observe outgrowth of cells derived from the inner cellular mass and trophectoderm with a light microscope over 7 days (blastocysts were isolated on day 0). Mutant and control blastocysts attached to the plate at high frequency. Cells derived from the inner cellular mass grew continuously for control but not mutant attached embryos (FIG. 4A, B). The number of trophoblast-like cells was the same for both mutant and control attached embryos (30–45 cells).

Analysis of rad51M1−/− embryos in utero and in tissue culture demonstrated reduced cell proliferation. Mutant cells were abnormal in embryos at the first time point observed by histology (day 5.5) demonstrating problems occurred earlier. However, most mutant embryos developed to the early egg cylinder stage in spite of the severe cellular phenotype. It is possible that a maternal component briefly rescued mutant preimplantation embryos. MmRad51 was shown to be expressed at high levels in the adult ovary (Morita et al., 1993) and the protein was localized to oocytes during meiosis (Ashley et. al., 1995) suggesting the presence of a maternal component.

Since MmRad51 is homologous to the recombinational repair proteins RecA and ScRad51 it is possible that decreased proliferation was due to a defect in DNA repair.

6.8. rad51M1 Mutant Cells are Hypersensitive to γ-Radiation

The role of MmRad51 in repairing DNA damage generated by γ-radiation was investigated in trophoblast-like cells derived from 3.5 day embryos isolated after heterozygous matings. The isolated blastocysts were exposed to 0, 200 and 400 RadS and then allowed to attach to tissue culture plates (day 0). Seven days later, the number of trophoblast-like cells were counted. There were 30–45 trophoblast-like cells without exposure to radiation for both control and mutant attached embryos (11 control and 4 mutant embryos observed; FIG. 4A, B). The control trophoblast-like cells were unaffected after exposure to 200 RadS (19 control embryos; FIG. 4C). However, the mutant trophoblast-like cells were reduced by 60–70% in number (the range was 10–17 cells for 7 mutant embryos; FIG. 4D). There was a slight reduction in trophoblast-like cell number when the control blastocysts were exposed to 400 RadS (the range was 20–34 cells for 11 control embryos). However, the mutant embryos failed to hatch and attach to the plate (three mutant embryos observed). These were the only floating embryos, and failure to hatch was shown to correlate with a dose-dependent response to radiation similar to outgrowth of trophoblast-like cells (Goldstein et al., 1975, Rad. Res. 62:276–287).

rad51M1−/− trophoblast-like cells were hypersensitive to γ-radiation. This demonstrated that MmRad51 may function to repair damaged DNA. Therefore, it is possible that the reduced cell proliferation and increased programmed cell death observed in mutant embryos and cells was due to unrepaired genetic damage.

6.9. rad51M1−/− Cells Have Reduced DNA Content

To measure the nuclear genetic content in cells, DNA was stained with a fluorescent dye, acridine orange, and fluorescence emission was measured with a fluorescent microscope. Cells derived form three control day 7.5 embryos were observed individually. The range of exposure time was between 0.10–0.61 seconds for 48 control cells. The time of exposure for 44% of these cells was concentrated between 0.21–0.30 seconds. Cells derived from three mutant day 7.5 embryos were observed. The range of exposure time was between 0.15–2.82 seconds for 37 mutant cells. The time of exposure for 689% of the mutant cells was concentrated between 0.15–0.67 seconds, and for 32% of the mutant cells was between 0.93–2.82 seconds (far out of the range for controls). Low level of fluorescence, reflected by long exposure time, indicated decreased DNA content in mutant cells. DNA content may be lost during programmed cell death; however, only two mutant cells appeared apoptotic (condensed chromatin; Graham et al., 1993, Devel. 119:233–245).

The DNA content was directly observed by metaphase spreads performed on cells disaggregated from day 7.5 embryos after 2 hours of colcemide treatment in utero. Three control embryos were observed individually, and 5 mutant embryos were combined. Mitotic spreads were observed for about half the control cells. The normal diploid number of chromosomes (40) was observed for 60 out of 60 cells (FIG. 5A). Unlike the control cells, the vast majority of mutant cells were not in mitosis. Only 10 metaphase spreads were observed out of 300 cells, one had the normal chromosome number and nine had a little more than half the chromosome number (22–28; FIG. 5B). Therefore, most of the mitotically dividing mutant cells, displayed multiple chromosome loss. It is possible that a cell cycle response to unrepaired DNA damage hindered cell proliferation, induced programmed cell death and promoted multiple chromosome loss.

6.10. rad51M1−/− Embryos Survive Longer in a p53 Mutant Background p53 is commonly believed to be central in delaying DNA replication and stimulating programmed cell death in response to DNA damage, including damage induced by γ-radiation (reviewed by Ko and Prives, 1996, Genes & Dev. 10:1054–1072). The rad51M1 mutation was crossed into a p53 mutant background (Donehower et al., 1992, Nature 356:215–221). There were no rad51M1−/− mice produced out of 41 progeny from a double heterozygote cross or out of 66 progeny from a p53−/− rad51M1+/− X p53+/−, rad51M1+/− cross. The expected number of p53−/−, rad51M1−/− mice was 11, demonstrating the rad51M1 lethal phenotype was not rescued in a p53 mutant background.

rad51M1 mutant embryos were observed in a p53 mutant background. Development of the rad51M1mutant embryos was not observed to change in a p53+/− background (Table II). However, rad51M1 mutant embryos appeared grossly normal by day 7.5 and were only slightly smaller than control embryos by day 8.5 in a p53−/− background (FIG. 6). By day 9.5, a double-mutant embryo did not increase in size after day 8.5 and was much smaller than controls. The head fold had clearly formed in the double-mutant embryos demonstrating a significant advance in proliferation and development as compared to the rad51M1 mutants in a p53 wild-type background.

TABLE II

Genotype and Gross Morphology for radm1 and p53 Mutations.

| MmRAD51 | +/+ | | +/− | | −/− | |
|---|---|---|---|---|---|---|
| p53 | +/− | −/− | +/− | −/− | +/− | −/− |
| 7.5 d.p.c. | 0 | 1(N) | 0 | 4(N) | 0 | 1(N) |
| 8.5 d.p.c. | 2 | 4(N) | 9(N) | 12(N) | 5(R) | 6(S) |
| 9.5 d.p.c. | 0 | 1(N) | 0 | 4(N) | 0 | 1(S) |

N - normal
S - small
R - resorbed

Murine embryonic fibroblasts (MEF) derived from double-mutant and control embryos were observed in tissue culture (controls were rad51M1+/+ or rad51M1+/− in a p53−/− background). Proliferation was measured in three 8.5 day double-mutant and 11 control MEF. The embryos were initially plated onto a 15 mm plate. The double-mutant MEF, unlike the controls, did not proliferate after 6 days and failed to form a confluent monolayer. The estimated number of cells was about 160, 330 and 1120 for the three double-mutant MEF and about 1×10⁴ for the control MEF. The double-mutant and control MEF were passaged at low density to observe colony formation. The cells were counted the next day and 14 days later. The number of double-mutant MEF decreased from 40–16, 84–16 and 280–48 and no colonies were observed, not even four cell colonies. Colonies frequently formed for all of the controls plated at a similar density (data not shown). MEF derived from one double-mutant and five control day 9.5 embryos were observed. Again the double-mutant MEF failed to proliferate and did not form a confluent monolayer, unlike the five controls. An acridine orange stain failed to demonstrate condensed chromatin, characteristic of programmed cell death, in either the double-mutant or control MEF (data not shown). Inability to proliferate and form colonies suggests these cells are prematurely senescent (Campisi, 1996, Cell 84:497–500). In addition, these cells appear senescent.

6.11. Screen for Rescue of Proliferation Defect in Mmrad51 p53 Double Mutant Embryonic Fibroblasts Embryonic fibroblasts mutant for MmRad51 and p53 will be used to screen for genetic mutations that rescue the proliferation defect. The mutations may be made by a variety of techniques and the particular technique employed to make the mutations is not important. Examples of methods to make mutations is to expose the cells to DNA damaging agents, preferably agents that do not generated double-strand breaks because it is likely that double-strand breaks will be lethal to these cells. Another method is to infect with retrovirus because the integration of the retrovirus may introduce mutations.

Another approach for rescuing proliferation is to ectopically express transgenes in the fibroblasts mutant for MmRad51 and p53. A variety of expression libraries may be used and the particular kind of library is unimportant.

Another approach to rescue the proliferation is to induce over expression of endogenous genes in the fibroblasts mutant for MmRad51 and p53. A variety of techniques may be used and the particular kind of technique is unimportant.

Another approach to rescue proliferation is to mutate genes by antisense technology in fibroblasts mutant for MmRad51 and p53. A variety of techniques may be used and the particular kind of technique is unimportant.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed:

1. A mouse cell heterozygous for a mutation engineered into the MmRad51 gene, wherein in a homozygous state said mutation results in a functionally deficient MmRad51 gene and a cellular phenotype of decreased cell proliferation followed by cell death and chromosome loss.

2. The cell of claim 1, said cell being an embryonic stem cell.

3. The cell of claim 1, said cell being an embryonic fibroblast.

4. A mouse cell heterozygous for a mutation engineered into the MmRad51 gene and for a mutation engineered into the p53 gene, wherein in a homozygous state the mutations result in a functionally deficient MmRad51 gene and a functionally deficient p53 gene, and wherein the mutations further result in a less severe cellular phenotype of decreased cell proliferation followed by cell death and chromosome loss as compared to the cellular phenotype of a mouse cell homozygous for the mutation engineered into the MmRad51 gene in the absence of the mutation in the p53 gene.

5. The cell of claim 4, said cell being an embryonic stem cell.

6. The cell of claim 4, said cell being an embryonic fibroblast.

7. A transgenic mouse whose genome is heterozygous for a mutation engineered into the MmRad51 gene, wherein in a homozygous state the mutation results in a functionally deficient MmRad51 gene and a cellular phenotype of decreased cell proliferation followed by cell death and chromosome loss.

8. A mouse embryonic fibroblast isolated from the transgenic mouse of claim 7.

9. A transgenic mouse whose genome is heterozygous for a mutation engineered into the MmRad51 gene and for a mutation engineered into the p53 gene, wherein in a homozygous state the mutations result in a functionally deficient MmRad51 gene and a functionally deficient p53 gene, and wherein the mutations further result in a less severe cellular phenotype of decreased cell proliferation followed by cell death and chromosome loss as compared to the cellular phenotype of a mouse cell homozygous for the mutation engineered into the MmRad51 gene in the absence of the mutation in the p53 gene.

10. A mouse embryonic fibroblast isolated from the transgenic mouse of claim 9 whose genome is heterozygous for the mutation engineered into the MmRad51 gene and for the mutation engineered into the p53 gene.

11. A method of screening for mutations that rescue proliferation of MmRad51/p53 double-mutant mouse embryonic fibroblasts, comprising the steps of:

(a) providing MmRad51/p53 double-mutant embryonic fibroblasts exhibiting a cellular phenotype of decreased cell proliferation followed by cell death and chromosome loss;

(b) growing the fibroblasts of step (a);

(c) identifying the fibroblasts of step (b) with an increased capacity to proliferate; and (d) identifying a mutation in the fibroblasts of step (c), wherein said mutation rescues proliferation of the MmRad51/p53 double-mutant mouse embryonic fibroblasts.

12. A method of screening for the overexpression of exogenous genes or endogenous genes that rescue proliferation of MmRad51/053 double-mutant mouse embryonic fibroblasts, comprising the steps of:

(a) inducing the overexpression of an exogenous or endogenous gene in MmRad51/p53 double-mutant embryonic fibroblasts exhibiting a cellular phenotype of decreased cell proliferation followed by cell death and chromosome loss;

(b) growing the fibroblasts of step (a) which overexpress the exogenous or endogenous gene;

(c) identifying the fibroblasts of step (b) with an increased capacity to proliferate; and (d) identifying an exogenous or endogenous gene that is being overexpressed in the fibroblasts of step (c), wherein the overexpression of said exogenous or endogenous gene rescues proliferation of the MmRad51/p53 double-mutant mouse embryonic fibroblasts.

13. A method of screening for ectopic expression of exogenous genes or endogenous genes that rescue the proliferation of MmRad51/p53 double-mutant mouse embryonic fibroblasts, comprising the steps of:

(a) inducing ectopic expression of an exogenous or endogenous gene in MmRad1/p53 double-mutant embryonic fibroblasts exhibiting a cellular phenotype of decreased cell proliferation followed by cell death and chromosome loss;

(b) growing the fibroblasts of step (a) which ectopically express the exogenous or endogenous gene;

(c) identifying the fibroblasts of step (b) with an increased capacity to proliferate; and (d) identifying an exogenous or endogenous gene that is being ectopically expressed in the fibroblasts of step (c), wherein the ectopic expression of said exogenous or endogenous gene rescues proliferation of the MmRad51/p53 double-mutant mouse embryonic fibroblasts.

14. A mouse cell homozygous for a mutation engineered into the MmRad51 gene, wherein said mutation results in a functionally deficient MmRad51 gene and a cellular phenotype of decreased cell proliferation followed by cell death and chromosome loss.

15. The cell of claim 14, said cell being an embryonic stem cell.

16. The cell of claim 14, said cell being an embryonic fibroblast.

17. A mouse cell homozygous for a mutation engineered into the MmRad51 gene and for a mutation engineered into the p53 gene, wherein the mutations result in a functionally deficient MmRad51 gene and a functionally deficient p53 gene, and wherein the mutations further result in a less severe cellular phenotype of decreased cell proliferation followed by cell death and chromosome loss as compared to the cellular phenotype of a mouse cell homozygous for the mutation engineered into the MmRad51 gene in the absence of the mutation in the p53 gene.

18. The cell of claim 17, said cell being an embryonic stem cell.

19. The cell of claim 17, said cell being an embryonic fibroblast.

20. A transgenic mouse embryo whose genome is homozygous for a mutation engineered into the MmRad51 gene, wherein said mutation results in a functionally deficient MmRad51 gene and a cellular phenotype of decreased cell proliferation followed by cell death and chromosome loss.

21. A mouse embryonic fibroblast isolated from the mouse embryo of claim 20.

22. A transgenic mouse embryo whose genome is homozygous for a mutation engineered into the MmRad51 gene and for a mutation engineered into the p53 gene, wherein the mutations result in a functionally deficient MmRad51 gene and a functionally deficient p53 gene, and wherein the mutations further result in a less severe cellular phenotype of decreased cell proliferation followed by cell death and chromosome loss as compared to the cellular phenotype exhibited by cells of a transgenic mouse embryo whose genome is homozygous for the mutation engineered into the MmRad51 gene in the absence of the mutation in the p53 gene.

23. A mouse embryonic fibroblast isolated from the mouse embryo of claim 22 whose genome is homozygous for the mutation engineered into the MmRad51 gene and for the mutation engineered into the p53 gene.

* * * * *